United States Patent [19]

Slepian et al.

[11] Patent Number: 5,213,580
[45] Date of Patent: May 25, 1993

[54] BIODEGRADABLE POLYMERIC ENDOLUMINAL SEALING PROCESS

[75] Inventors: Marvin J. Slepian, Cleveland Heights, Ohio; Anton Schindler, Durham, N.C.

[73] Assignee: Endoluminal Therapeutics, Inc., Tucson, Ariz.

[21] Appl. No.: 857,700

[22] Filed: Mar. 25, 1992

Related U.S. Application Data

[63] Continuation of Ser. No. 593,302, Oct. 3, 1990, abandoned, which is a continuation of Ser. No. 235,998, Aug. 24, 1988, abandoned.

[51] Int. Cl.$^5$ ............................. A61F 2/04; A61F 2/06
[52] U.S. Cl. ............................. 623/1; 623/11; 623/66
[58] Field of Search ........................... 623/1, 66, 12, 13

[56] References Cited

U.S. PATENT DOCUMENTS

| | | |
|---|---|---|
| 3,868,956 | 3/1975 | Alfidi et al. |
| 3,880,158 | 4/1975 | Gurney |
| 3,987,000 | 10/1976 | Gleichenhagen et al. |
| 4,140,126 | 2/1979 | Choudhury .................. 623/1 X |
| 4,156,067 | 5/1979 | Gould |
| 4,272,518 | 6/1981 | Moro et al. |
| 4,377,010 | 3/1983 | Fydelor et al. |
| 4,459,252 | 7/1984 | MacGregor |
| 4,503,569 | 3/1985 | Dotter |
| 4,553,545 | 11/1985 | Maass et al. |
| 4,580,568 | 4/1986 | Glanturco |
| 4,610,662 | 9/1986 | Weikl et al. |
| 4,655,746 | 4/1987 | Daniels et al. |
| 4,665,771 | 4/1987 | Wallsten |
| 4,674,506 | 6/1987 | Alcond .................. 623/66 X |
| 4,690,684 | 9/1987 | McGreevy et al. |
| 4,701,509 | 10/1987 | Sun et al. |
| 4,702,917 | 10/1987 | Schindler .................. 424/422 |
| 4,733,665 | 3/1988 | Palmaz |
| 4,799,479 | 1/1989 | Spears |
| 4,820,298 | 4/1989 | Leveen et al. .................. 623/1 |

FOREIGN PATENT DOCUMENTS 0183372 10/1985 European Pat. Off. .................. 623/1

OTHER PUBLICATIONS

Peter Barath, M.D. et al., "Combined Angioplasty and Vascular Stenting by a Novel Heat-Expandable Thermoplastic Device" JACC vol. 11, No. 2-Feb. 1988:65A.
Sandra Blakeslee, "Race Is On to Develop Nonsurgical Ways To Unclog Arteries", The New York Times, HEALTH, Jul. 28, 1988.
"Improved Intravascular Delivery of Drug Via a Polyethylene Jet Catheter", John W. Boretos, The 13th Annual Meeting of the Society for Biomaterials, Jun. 2-6, 1987, New York, N.Y. USA, 128.
"Local Enzymatic Treatment of Atherosclerotic Plaques", T. Kerenyi, V. Merkel, Z. Szabolcs, A. Pusztai, and G. Nadasy, Experimental and Molecular Pathology 49, 330-338 (1988).

*Primary Examiner*—David Isabella
*Assistant Examiner*—Debra S. Brittingham
*Attorney, Agent, or Firm*—Brumbaugh, Graves, Donohue & Raymond

[57] ABSTRACT

A novel process for paving or stabilizing sealing the interior surface of a body vessel or organ by entering the interior of the vessel or organ and applying a polymer to the interior surface of the vessel or organ.

17 Claims, 3 Drawing Sheets

BIODEGRADABLE POLYMERIC ENDOLUMINAL SEALING PROCESS

This is a continuation of Ser. No. 593,302, filed Oct. 3, 1990, now abandoned, which is a continuation of Ser. No. 235,998, filed Aug. 24, 1988, now abandoned.

BACKGROUND OF THE INVENTION

This invention relates to a novel method for the in vivo paving and sealing of the interior of organs having hollow or tubular geometry for example, blood vessels such as arteries or veins. Often times, this geometry has functional significance such as in the facilitation of fluid or gas transport (blood, urine, lymph, oxygen or respiratory gases) or cellular containment (ova, sperm). Disease processes often times affect these organs or their components by encroaching upon, obstructing or otherwise reducing the cross-sectional area of the hollow or tubular elements. Additionally, other disease processes may violate the native boundaries of the hollow organ and thereby affect its barrier function and/or containment ability. The ability of the organ or structure to properly function is then severely compromised. A good example of this phenomena can be seen by reference to the coronary arteries.

Coronary arteries, or arteries of the heart, perfuse the actual cardiac muscle with arterial blood. They also provide essential nutrients and allow for metabolic waste and gas exchange. These arteries are subject to relentless service demands for continuous blood flow throughout the life of the patient.

Despite their critical life supporting function, coronary arteries are often subject to attack through several disease processes, the most notable being atherosclerosis or hardening of the arteries. Throughout the life of the patient, multiple factors contribute to the development of microscopic and/or macroscopic vascular lesions known as plaques.

The development of a plaque lined vessel typically leads to an irregular inner vascular surface with a corresponding reduction of vessel cross-sectional area. The progressive reduction in cross-sectional area compromises flow through the vessel. For example, the effect on the coronary arteries, is a reduction in blood flow to the cardiac muscle. This reduction in blood flow, with corresponding reduction in nutrient and oxygen supply, often results in clinical angina, unstable angina or myocardial infarction (heart attack) and death. The clinical consequences of the above process and its overall importance are seen in that atherosclerotic coronary artery disease represents the leading cause of death in the United States today.

Historically, the treatment of advanced atherosclerotic coronary artery disease i.e. beyond that amenable to therapy via medication alone, involved cardiothoracic surgery in the form of coronary artery bypass grafting (CABG). The patient is placed on cardio-pulmonary bypass and the heart muscle is temporarily stopped. Repairs are then surgically affected on the heart in the form of detour conduit grafted vessels providing blood flow around obstructions. While CABG has been perfected to be quite effective it carries with it inherent surgical risk and requires a several week, often painful recouperation period. In the United States alone approximately 150-200 thousand people are subjected to open heart surgery annually.

In 1977 a major advance in the treatment of atherosclerotic coronary artery disease occurred with the introduction of a technique known as Percutaneous Transluminal Coronary Angioplasty (PTCA). PTCA involves the retrograde introduction, from an artery in the arm or leg, up to the area of vessel occlusion, of a catheter with a small dilating balloon at its tip. The catheter is snaked through the arteries via direct fluoroscopic guidance and passed across the luminal narrowing of the vessel. Once in place the catheter ballon is inflated to several atmospheres of pressure. This results in "cracking", "plastic" or otherwise mechanical deformation of the lesion or vessel with a subsequent increase in the cross-sectional area. This in turn reduces obstruction, and trans-lesional pressure gradients and increases blood flow.

PTCA is an extremely effective treatment with a relatively low morbidity and is rapidly becoming a primary therapy in the treatment of atherosclerotic coronary disease throughout the United States and the world. By way of example, since its introduction in 1977, the number of PTCA cases now exceeds 150,000 per annum in the United States and, for the first time in 1987, surpassed the number of bypass operations performed. Moreover, as a result of PTCA, emergency coronary artery bypass surgery is required in less than four percent of patients. Typically, atherosclerosis is a diffuse arterial disease process exhibiting simultaneous patchy involvement in several coronary arteries. Patients with this type of widespread coronary involvement, while previously not considered candidates for angioplasty, are now being treated due to technical advances and increased clinical experience.

Despite the major therapeutic advance in the treatment of coronary artery disease which PTCA represents, its success has been hampered by the development of vessel renarrowing or reclosure post dilation. During a period of hours or days post procedure, significant total vessel reclosure may develop in up to 10% of cases. This is referred to as "abrupt reclosure". However, the more common and major limitation of PTCA, is the development of progressive reversion of the vessel to its closed condition, negating any gains achieved from the procedure.

This more gradual renarrowing process is referred to as "restenosis." Post-PTCA follow-up studies report a 10–50% incidence (averaging approximately 30%) of restenosis in cases of initially successful angioplasty. Studies of the time course of restenosis have shown that it is typically an early phenomenon, occurring almost exclusively within the six months following an angioplasty procedure. Beyond this six-month period, the incidence of restenosis is quite rare. Despite recent pharmacologic and procedural advances, little success has been achieved in preventing either abrupt reclosure or restenosis post-angioplasty.

Restenosis has become even more significant with the increasing use of multi-vessel PTCA to treat complex coronary artery disease. Studies of restenosis in cases of multi-vessel PTCA reveal that after multi-lesion dilatation, the risk of developing at least one recurrent coronary lesion range from 26% to 54% and appears to be greater than that reported for single vessel PTCA. Moreover, the incidence of restenosis increases in parallel with the severity of the preangioplasty vessel narrowing. This is significant in light of the growing use of PTCA to treat increasingly complex multi-vessel coronary artery disease.

The 30% overall average restenosis rate has significant costs including patient morbidity and risks as well as medical economic costs in terms of follow-up medical care, repeat hospitalization and recurrent catherization and angioplasty procedures. Most significantly, prior to recent developments, recurrent restenosis following multiple repeat angioplasty attempts could only be rectified through cardiac surgery with the inherent risks noted above.

In 1987 a mechanical approach to human coronary artery restenosis was introduced by Swiss investigators referred to as, "Intracoronary Stenting". An intracoronary stent is a tubular device made of fine wire mesh, typically stainless steel. The Swiss investigators utilized a stent of the Wallsten design as disclosed and claimed in U.S. Pat. No. 4,655,771. The device can be configured in such a manner as to be of low cross-sectional area. In this "low profile" condition the mesh is placed in or on a catheter similar to those used for PTCA. The stent is then positioned at the site of the vascular region to be treated. Once in position, the wire mesh stent is released and allowed to expand to its desired cross-sectional area generally corresponding to the internal diameter of the vessel. Similar solid stents are also disclosed in U.S. Pat. No. 3,868,956 to Alfidi et al.

The metal stent functions as a permanent intravascular scaffold. By virtue of its material properties, the metal stent provides structural stability and direct mechanical support to the vascular wall. Stents of the Wallsten design are self-expanding due to their helical "spring" geometry. Recently, U.S. investigators introduced slotted steel tubes and extended spring designs. These are deployed through application of direct radial mechanical pressure conveyed by a balloon at the catheter tip. Such a device and procedure are claimed in U.S. Pat. No. 4,733,665 to Palmaz. Despite the significant limitations and potentially serious complications discussed below, this type of stenting has been successful with an almost 100% acute patency rate and a marked reduction in the restenosis rate.

The complications associated with permanent implants such as the Palmaz device result from both the choice of material, i.e., metal or stainless steel, as well as the inherent design deficiencies in the stenting devices. The major limitation lies in the permanent placement of a non-retrivable, non-degradable, foreign body in a vessel to combat restenosis which is predominately limited to the six-conveyed month time period post-angioplasty. There are inherent, significant risks common to all permanent implant devices. Moreover, recent studies have revealed that, atrophy of the media, the middle arterial layer of a vessel, may occur as a specific complication associated with metal stenting due to the continuous lateral expansile forces exerted after implantation.

These problems are even more acute in the placement of a permanent metallic foreign body in the vascular tree associated with the cardiac muscle. Coronary arteries are subjected to the most extreme service demands requiring continuous patency with unimpeded flow throughout the life of the patient. Failure in this system will lead to myocardial infarction (heart attack) and death. In addition, the torsional and other multi-directional stresses encountered in the heart due to its continuous oscillatory/cyclic motion further amplifies the risks associated with a permanent, stiff metallic intra-arterial implant in the coronary bed.

It has been observed that, on occasion, recurrent intravascular narrowing has occurred post-stent placement in vessels during a period of several weeks to months. Typically, this occurs "peri-stent" , i.e., immediately up or down stream from the stent. It has been suggested that this may relate to the significantly different compliances of the vessel and the stent, sometimes referred to as "compliance mismatch". Aside from changes in compliance another important mechanism leading to luminal narrowing above and below the stent may be the changes in shear forces and fluid flows encountered across the sharp transitions of the stentvessel interface. Further supporting evidence has resulted from studies of vascular grafts which reveal a higher incidence of thrombosis and eventual luminal closure also associated with significant compliance mismatch.

To date known stents designs, i.e. tubular, wire helical or spring, scaffold design have largely been designed empirically without consideration or measurement of their radial stiffness. Recent studies measuring the relative radial compressive stiffness of known wire stents, as compared to physiologically pressurized arteries, have found them to be much stiffer than the actual biologic tissue. These studies lend support to the concept of poor mechanical biocompatibility of currently available stents.

Conventional metal stenting is severely limited since it is device dependent and necessitates a myriad of individual stents as well as multiple deployment catheters of varying lengths and sizes to accommodate individual applications. Additionally, metal stents provide a relatively rigid nonflexible structural support which is not amenable to a wide variety of endoluminal geometries, complex surfaces, luminal bends, curves or bifurcations.

These identified risks and limitations of metal stents have severely limited their utility in coronary artery applications. As of 1988, a partial self-imposed moratorium exists in the use of helical metal stents to treat human coronary artery diseases. Presently in the United States, a spring-like wire coil stent has been approved only for short term use as an emergency device for patients with irreparably closed coronary arteries following failed PTCA while in transit to emergency bypass surgery. An alternative to the use of stents has now been found which has broad applications beyond use in coronary artery applications for keeping hollow organs open and in good health.

SUMMARY OF THE INVENTION

The present invention relates to a novel technique, of polymeric endoluminal paving and sealing (PEPS), in which the interior surfaces of hollow organs or organ systems or components are paved and sealed with varying thicknesses of a polymer which is preferably biodegradable.

DETAILED DESCRIPTION OF THE INVENTION

Figure 1:
FIG. 1 shows an amorphous geometry of the PEPS polymer.

PEPS is a unique customizable process, which can be utilized as a given biological or clinical situation dictates. Preferably PEPS utilizes biodegradable polymers, with specific degradation, lifespan and properties, which can be applied in custom designs, with varying thicknesses, lengths, and three-dimensional geometries (e.g. spot, stellate, linear, cylindrical, arcuate, spiral) FIGS. 1-8. Further, PEPS may be used to apply polymer to the inner surfaces of hollow, cavernous, or tubular biological structures in either single or multiple polymer layer configurations.

The technique of PEPS involves the application of a polymer preferably a biodegradable polymer such as polycaprolactone, either alone or mixed with other biodegradable polymers, which may optionally contain various pharmaceutical agents for controlled sustained release of the pharmaceutical or for selective soluble factor adsorption and trapping. The polymer is typically applied, to the inside of an organ surface employing combined thermal and mechanical means to manipulate the polymer. Although capable of being used during surgery, PEPS will generally be applied without the need for a surgical procedure using some type of catheter for example the known catheter technology described above for (PTCA). Current catheter technology will even allow the use of a single catheter with multiple balloons on lumens. The catheter should be of relatively low cross-sectional area. Typically a long thin tubular catheter through manipulated using fluoroscopic guidance can access deep into the interior of organ or vascular areas.

Specifically, the polymer may be deployed in the interior of the vessel or organ from the surface or tip of the catheter. Alternatively, the polymer could be positioned on a ballon such as a standard angioplasty ballon catheter. Additionally, the polymer could be applied by spraying, extruding or otherwise internally delivered via a long flexible tubular device consisting of as many lumens as a particular application may dictate.

In addition to arteries i.e. coronary, femeroiliac, carotid and vertebro-basilar, the PEPS process may be utilized for other applications such as paving the interior of veins, ureters, urethrae, bronchi, biliary and pancreatic duct systems, the gut, eye and spermatic and fallopian tubes. The sealing and paving of the PEPS process suggests other direct clinical applications even at the coronary level. This includes but is not limited to the treatment of abrupt vessel reclosure post PCTA, the "patching" of significant vessel dissection, the sealing of vessel wall "flaps", i.e. secondary to catheter injury or spontaneously occurring, the sealing of aneurysmal coronary dilations associated with various arteritidies. Further, PEPS provides intra-operative uses such as sealing of vessel anostomoses during coronary artery bypass grafting and the provision of a bandaged smooth polymer surface post endarterectomy.

Examples of some pharmaceuticals which could be combined with biodegradable polymers for use in PEPS in coronary artery applications are anti-thrombotic agents, e.g., prostacyclin and salicylates, thrombolytic agents e.g. streptokinase, urokinase, tissue plasminogen activator (TPA) and ASPAC, vasodilating agents i.e. nitrates, calcium channel blocking drugs, anti-proliferative agents i.e. colchicine and alkylating agents, intercalating agents, monoclonal antibodies directed against growth factors, anti-inflammatory agents i.e. steriods and NSAID's and other agents which may modulate vessel tone, function, arteriosclerosis, and the healing response to vessel or organ injury post intervention. In applications where multiple polymer layers are used different pharmacological agents could be used in different polymer layers.

This unique pharmaceutical delivery function of the PEPS process may be readily combined with "customizable" deployment geometry capabilities to accommodate the interior of a myriad of complex organ or vessel surfaces. Most importantly, this customized geometry is made from structurally stable yet biodegradable polymer. The ability to tailor the external shape of the deployed polymer through melted polymer flow into uneven surface interstices, while maintaining a smooth interior surface with good flow characteristics, will facilitate better structural support for a variety of applications including eccentric coronary lesions which by virtue of their geometry are not well bridged with conventional metal stents.

Polycaprolactone as disclosed and claimed in U.S. Pat. No. 4,702,917 to Schindler is an ideal bioabsorbable polymer for use in the PEPS process. Polycaprolactone possesses adequate mechanical strength being mostly crystalline even under quenching conditions. Despite its structural stability, polycaprolactone is much less rigid than the metals used in traditional stenting. This minimizes the risk of acute vessel wall damage from sharp or rough edges.

The rate of bioabsorption of polycaprolactone is ideal for the current application. The degradation process of this polymer has been well characterized with the primary degradation product being nonparticulate, nontoxic, 6-hydroxy hexanoic acid of low acidity. The time of biodegradation of polycaprolactone can be adjusted through the addition of various copolymers.

Polycaprolactone is a preferred polymer for use in the PEPS process because it has attained favorable clinical acceptability and is in the advanced stages of FDA approval. Polycaprolactone has a crystalline melting point of 60° C. and can be deployed in vivo via a myriad of techniques which facilitate transient heating and varying degrees of mechanical deformation or application as dictated by individual situations. This differs markedly from other bioabsorbable polymers such as polyglycolide and polylactide which melt at much higher temperatures of 180° C. and pose increased technical constraints as far as the delivery system affording polymer sculpting yet without deleterious tissue exposure to excessive temperatures or mechanical forces.

Although the invention is not limited to polycaprolactone, it is preferred for use in PEPS because it is a bioabsorbable non-crosslinked crystalline polymer which will go through a melt-recrystallization process by heating within a temperature range acceptable within the human body. Once polycaprolactone has been deployed its crystalline structure will maintain a constant outside diameter. This eliminates the risks often associated with known helical or spring metal stents which after being expanded in vivo have a tendency to further expand exerting increasing pressure on the vessel wall.

Vessel narrowing, if it does occur, tends to stabilize beyond the six month window following the initial procedure without further accelerated narrowing. Optimally, if a foreign support device or sealant material is to be introduced into the vessel it would need to exert its intended effect, principally during the period of healing and peak restenosis incidence. Accordingly, the nature of the polymeric material used will be a function of whether it assumes a coating, bandaging, shielding, bioabsorbtive, drug delivery, or mechanical support role. Further, the choice of polymer must appropriately balance the degree of structural and geometric integrity needed against the appropriate rate of biodegradation over the time period targeted to prevent restenosis.

Other bioabsorbable polymers could also be used either singly or in combination. Further polymers can be cross-linked with bis-caprolactone. By way of example, homopolymers and copolymers of glycolic acid, lactic acid, delta-valerolactone, epsilon-caprolactone, and p-dioxanone as well as their copolymers with caprolactone.

The polymer substrate used in PEPS may be fashioned, for example, out of extruded tubes of polycaprolactone and/or copolymers with an optional additive such as barium, iodine or tantalum salts for X-ray radioopacity. The initial predeployment design of the polymer will be dictated by the specific application based upon the final deployed physiological and pharmacological properties desired.

For coronary artery application predeployment tubes of about 10 to 20 mm in length and about 1 to 2 mm in diameter would be useful. The initial wall thickness of the resulting in vivo polymer layer may be varied depending upon the nature of the particular application. In general coating procedures require polymer layers of about 0.005 mm to 0.50 mm while layers which are designed to give structural support can vary from 0.05 mm to 5.0 mm.

The polymer tube walls may be processed prior to insertion with either laser or chemical etching, pitting, slitting or perforation depending upon the application. In addition the shape of any micro or macro perforation may be further geometrically modified to provide various surface areas on the inner versus outer seal surface. The surfaces of the predeployed polymer may be further modified with bound, coated, or otherwise applied agents, i.e., cyanoacrylates or biological adhesives such as those derived from fungal spores, the sea mussel or autologous fibrinogen adhesive derived from blood.

For PEPS applications involving the coronary arteries the polymer tubes if in an initial tubular configuration, should preferably have perforations or pores, of sized dictated by the particular application. This will ensure a symmetric expansion of the encasing polymeric sealant. By using a fragmented tubular polymer surface with corresponding expansions along predicted perforations (i.e., the slots) a significant mechanical stabililty is provided. In addition, this minimizes the amount of foreign material placed within the vessel.

Depending upon the polymer and pharmaceutical combination and the configuration, PEPS may be used to coat or bandage the organ inner surface with a thin adhesive partitioning polymer film or layer of about 0.005 mm to 0.50 mm. Biodegradable polymers thus applied to an internal organ or vessel surface will act as an adherent film "bandage." This improved surface, with desirable rheologic and adherence properties, facilitates improved fluid or gas transport in and through the body or lumen of the vessel or hollow organ structure and acts to reinstate violated native surfaces and boundaries.

The ultimate in vivo deployed geometry of the polymer dictates the final function of the polymer coating. The thinner applications allow the polymer film to function as a coating, sealant and/or partitioning barrier, bandage, and drug depot. Complex internal applications of thicker layers of polymer, such as intra-vessel or intra-luminal applications, may actually provide increased structural support and depending on the amount of polymer used in the layer may actually serve in a mechanical role to maintain vessel or organ potency.

For example, lesions which are comprised mostly of fibromuscular components have a high degree of viscoelastic recoil. These lesions would require using the PEP process to apply an intraluminal coating of greater thickness and extent so as to impart more structural stability thereby resisting vessel radial compressive forces. The PEPS process in this way provides structural stability and is generally applicable for the maintenance of the intraluminary geometry of all tubular biological organs or substructure. It may be used in this way following the therapeutic return of normal architecture associated with either balloon dilation (PTCA), atherectomy, lesion spark, thermal or other mechanical erosion, "G-lazing", welding or laser recanalization.

An important feature of the PEPS technique is the ability to customize the application of the polymer to the internal surface of a vessel or organ as dictated by the particular application. This results in a variety of possible geometries of polymer as well as a variety of forms. These multi-geometry, multi-form polymer structures may be adjusted to correspond to particular functions. (FIGS. 1-8)

Figure 2:
FIG. 2 shows a stellate geometry of the PEPS polymer.
Figure 3:
FIG. 3 shows a linear feathered polymer strip applied to "one" wall.
Figure 4:
FIG. 4 shows a large patch of sprayed on polymer material.
Figure 5:
FIG. 5 shows a porous tubular form geometry.
Figure 6:
FIG. 6 shows a spot geometry of the PEPS process.
Figure 7:
FIG. 7 shows a spiral form application of the PEPS process.
Figure 8:
FIG. 8 shows an arcuate (radial, arc) patch geometry of the PEPS polymer.

With particular reference to FIGS. 1-8 the PEPS process may be affectuated so that the focal application of polymer to the vessel or organ results in either an amorphous geometry, FIG. 1, stellate geometry, FIG. 2, or spot geometry, FIG. 6. Additional geometries could include a linear feathered polymer strip applied to a particular area of the vessel wall as shown in FIG. 3. FIG. 4 shows a large patch of polymer which can be sprayed on using a variety of known techniques. Another form of the PEPS application to be utilized in instances, e.g., where structural stability need be imparted to the vessel would be the porous tubular form shown in FIG. 5. Other types of PEPS applications which would impart structural stability to the vessel would be the spiral form application shown in FIG. 7 where the arcuate (radial, arc) patch as shown in FIG. 8.

Conversely, in cases where the severely denuded lesions have irregular surfaces with less fibromuscular components, the PEPS process can be used to provide only a thin polymer film to act as a bandage.

The PEPS' process is significantly different and is conceptually an advance beyond stents and stenting in achieving vessel patency. Stents have been designed with the underlying primary function of providing a relatively stiff structural support to resist post PTCA, vessel reclosure caused by the vessel's spring-like characteristics. It has been increasingly demonstrated that cellular and biochemical mechanisms as opposed to physical "spring-like" recoil, are of a much greater significance in causing vessel reclosure and PEPS addresses these mechanisms.

The specific object and features of the PEPS process are best understood by way of illustration with reference to the following examples and figures.

Figure 12:
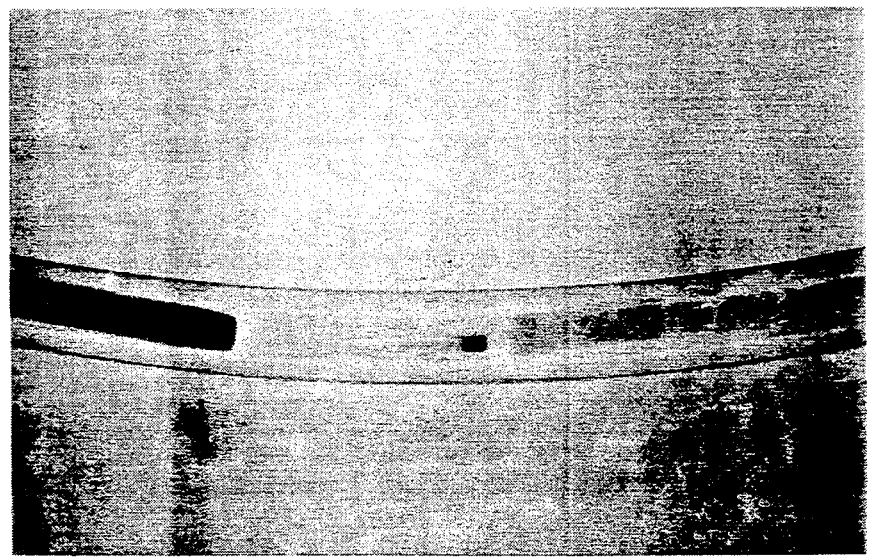
FIG. 12 shows a inflated distal occlusion catheter, the polymer substrate surrounded by hot saline solution, and the initial inflation of the delivery balloon thereby expanding the polymer tube.

The invention may be readily understood through a description of an experiment performed in vitro using a mock blood vessel made from transparent plastic tubing using a heat-balloon type deployment catheter and reference to FIG. 12.

EXAMPLE 1

A balloon delivery catheter is first positioned in the vessel at the area of the occlusion. Before insertion, a polycaprolactone polymer tube, with additives to aid X-ray radioopacity or with drugs or surface adhesive, is placed in a low profile condition surrounding a ballon at the distal end of the delivery catheter. The delivery catheter with the polycaprolactone tube is then inserted balloon end first into the mock vessel to the area to be repaired.

A separate occlusion catheter was employed to restrict "blood" flow through the vessel. The distal end of the occlusion catheter is inflated to create a stagnant column of "blood" in the vessel around the balloon delivery catheter and polycaprolactone tube. Saline solution at about 60°-80° C. is injected through a lumen in the occlusion catheter into the area surrounding the delivery catheter, balloon and polycaprolactone tube. Once the polycaprolactone tube becomes pliable, the delivery catheter balloon is inflated to push the polycaprolactone tube out against the interior wall thereby sealing and/or paving the vessel.

Figure 9:
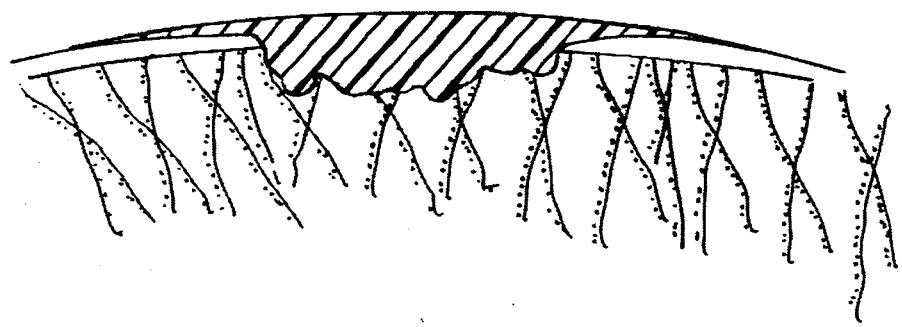
FIG. 9 shows the deployed polymer sealed vessel.

The polycaprolactone expands and/or flows, conforming to the inner surface of the vessel, flowing into and filling in surface irregularities thereby creating a "tailored" fit. (FIG. 9) Further, the deployed interior surface of the PEPS polymer is smooth providing an increased vessel (lumen) cross-section diameter and a theologically advantageous surface with improved blood flow.

The deployment catheter balloon is then deflated leaving the expanded polycaprolactone tube in place. The balloon section of the occlusion catheter is deflated, blood flow is allowed to return to normal and the deployment catheter is removed leaving the recrystalized polycaprolactone tube in place.

Over the course of time the polycaprolactive seal will become covered with a proteinaceous biologic thin film coat. Depending upon the exact seal chemical composition, the polymer will then biodegrade, at a predetermined rate and will "dissolve" into the bloodstream or be absorbed into the vessel wall. While in intimate contact with the vessel wall pharmacological agents if embedded or absorbed in the polycaprolactone will have a "downstream" effect if released slowly into the bloodstream or will have a focal effect on the blood vessel wall, thereby facilitating healing of the angioplasty site, controlling or reducing exuberant media smooth muscle cell proliferation, promoting effective lesion endothelialyation and reducing lesion thrombogenicity.

EXAMPLE 2

Polycaprolactone in an initial macroporous tubular configuration was placed in a low profile form in bovine coronary arteries and canine carotid arteries using a standard angioplasty balloon catheter device. In the process of deployment the vessels were purposely overextended and sealed through thermal and mechanical deformation of the polymer. (FIGS. 10, 11, and 12) The thin film of polymer can be seen coating the inner surface of the sealed vessel with the vessel remaining erect. The predeployed polymer 50, the predeployed artery 52 with predeployed polymer placed within the postployed vessel 54 intimately sealed with adherent thin film postdeployed polymer 56 are also depicted. The vessel remained dilated because of the ability of the polymer to keep it fixed.

All polymer sealed vessels remained dilated with a thin layer of macroporous polymer providing a new barrier surface between the vessel lumen and the vessel wall constituents. The unsealed vessels did not remain dilated.

These examples demonstrate that the PEPS process may if desired provide polymer application with a large degree of surface area coverage and an effective polymer barrier shield. As such, this polymer barrier-shield may, if desired, impart sufficient structural stability to maintain a selected vessel diameter. The selected final vessel diameter at which a vessel is sealed is dictated by the particular physiological variables and therapeutic goals which confront the PEPS user.

Figure 10:
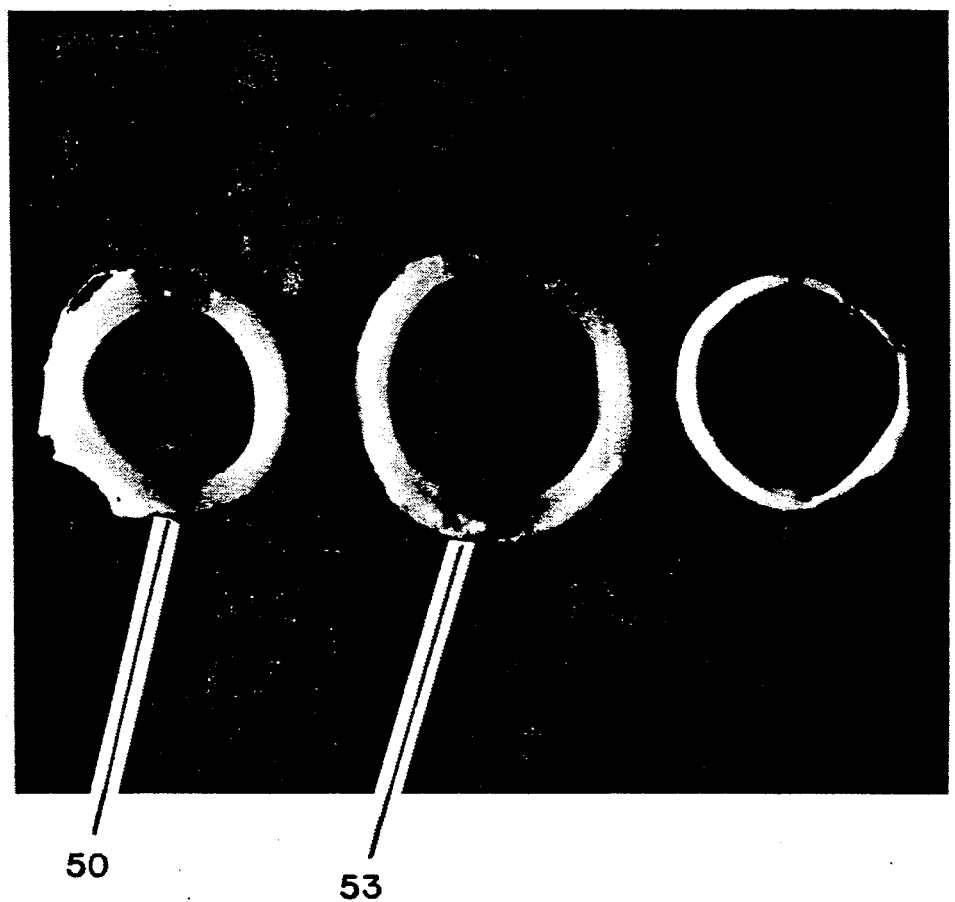
FIG. 10 shows the predeployed polymer alone, then within the vessel in predeployed form and postdeployed and geometrically altered polymer and vessel.
Figure 11:
FIG. 11 shows a predeployment low profile polymer as well as the postdeployment recrystallized and expanded polymer seal for use in PEPS.

The geometry of the pre and post PEPS application sites may be readily varied. PEPS may be used to merely coat an existing vessel or organ geometry. Alternatively, the PEPS process may be used to coat or impart structural stability to a vessel or organ the geometry of which was altered prior to the PEPS application. In addition, the PEPS process may itself alter the geometry of the vessel or organ by shaping the geometry. With reference to FIG. 10 this latter process was used to expand the vessel 53.

A superior attribute of the PEPS technique and the polymers which are employed is the significantly lower degree of compliance mismatch or similarities of stiffness (inverse of compliance) between the vessel and the polymer seal as compared to metal stents. The vessel damage from compliance mismatch discussed above may be eliminated by the PEPS process utilizing a variety of available polymers. Additionally, a greater degree of native vessel, versus stented region, compliance mismatch greatly modifies the characteristics of fluid wave transmission along the vessel with resultant change in local flow properties development of regional change in shear forces and a subsequent vessel wall hypertrophy which acts to reduce vessel cross-sectional area and reduces blood flow. Further, the lesser degree of compliance mismatch of the PEPS technique minimizes and then eliminates, upon dissolve, local flow abnormalities and up and downstream transition zone hypertrophy associated with metal stenting.

PEPS has the flexibility of being safely and effectively used prophylactically at the time of initial PTCA in selected patients or being incorporated as part of the original dilation procedure as a second stage prophylactic vessel surface "finishing" process. For example, the invasive cardiologist may apply the PEPS technique on a wide clinical basis after the first episodes of restenosis. In addition, because the PEPS technique significantly aids in the vascular healing process post intervention, it may be readily used prophylactically after initial angioplasty prior to any incidence of restenosis. This would free the patient from the risks of repeat intracoronary procedure as well as those associated with metal stenting.

We claim:

1. A process for paving or stabilizing an irregularly contoured interior surface of a body vessel or organ in an animal, including man, comprising introducing flowable polymeric material onto and filling said irregularly contoured interior surface of the vessel or organ and reconfiguring the polymeric material to form a layer of polymer, said polymer layer having an outer surface which conforms with and is affixed to the irregularly contoured interior surfaces of the vessel or organ and a smooth inner luminal surface.

2. A process as described in claim 1, wherein the polymeric material is a biodegradable polymer.

3. A process as described in claim 1 or 2 wherein the polymeric material is applied in a preshaped form to the interior surface of the vessel or organ.

4. A process as described in claim 2, wherein the layer of biodegradable polymer as applied has a thickness of about 0.005 mm to 0.50 mm, so as to create a thin layer.

5. A process as described in claim 2, wherein the layer of biodegradable polymer is about 0.05 mm to 5.0 mm so as to impart structural stability to the organ or vessel.

6. A process as described in claim 2 wherein the biodegradable polymer is selected from the group consisting of a homopolymer, a binary and ternary copolymer.

7. A process as described in claim 6 wherein the polymer is selected from the group consisting of glycolic acid, lactic acid, delta-valerolactone, p-dioxanone, and epsilon-caprolactone.

8. A process as described in claim 6 wherein the biodegradable polymer constitutes a blend of homopolymers or copolymers.

9. A process as described in claim 6 wherein the biodegradable polymer is cross-linked with a biscaprolactone.

10. A process as described in claim 2, wherein the biodegradable polymer is poly (epsilon-caprolactone).

11. A process as described in claim 2, wherein the polymer contains a pharmaceutical agent.

12. The process as described in claim 11, wherein multiple polymers containing various pharmacological agents are applied.

13. A process as described in claim 2 wherein the vessel is a coronary artery.

14. A process as described in claim 1, wherein a catheter is used to enter the interior of the vessel or organ and to apply the polymer layer.

15. A process for paving an irregularly contoured interior surface of a coronary artery in an animal, including man, comprising flowing poly(epsilon-caprolactone) onto the irregularly contoured interior surface of the artery and reconfiguring the poly(epsilon-caprolactone) to form a layer, said layer having an outer surface which conforms with and is affixed to the irregularly contoured interior surface of the artery and a smooth inner luminal surface.

16. A process as described in claim 15 wherein a catheter is used to introduce poly(epsilon-caprolactone) into the artery.

17. A process as described in claim 1 wherein the polymer is applied in such a manner as to shape the vessel or organ.

* * * * *